(12) United States Patent
Obradovic

(10) Patent No.: US 8,852,268 B2
(45) Date of Patent: Oct. 7, 2014

(54) STENT HAVING EXPANDABLE ELEMENTS

(75) Inventor: Milisav Obradovic, Loerrach (DE)

(73) Assignee: Bentley Surgical GmbH, Hechingen (DE)

( * ) Notice: Subject to any disclaimer, the term of this patent is extended or adjusted under 35 U.S.C. 154(b) by 186 days.

(21) Appl. No.: 13/391,730

(22) PCT Filed: Sep. 16, 2009

(86) PCT No.: PCT/DE2009/001306
§ 371 (c)(1),
(2), (4) Date: Feb. 22, 2012

(87) PCT Pub. No.: WO2011/032526
PCT Pub. Date: Mar. 24, 2011

(65) Prior Publication Data
US 2012/0158125 A1    Jun. 21, 2012

(51) Int. Cl.
*A61F 2/06* (2013.01)
*A61F 2/91* (2013.01)
*A61F 2/915* (2013.01)

(52) U.S. Cl.
CPC .......... *A61F 2/91* (2013.01); *A61F 2250/0082* (2013.01); *A61F 2002/91525* (2013.01); *A61F 2250/001* (2013.01); *A61F 2002/91575* (2013.01); *A61F 2250/0071* (2013.01); *A61F 2/915* (2013.01); *A61F 2002/91583* (2013.01); *A61F 2250/0018* (2013.01); *A61F 2210/0057* (2013.01)
USPC .......................................... 623/1.3; 623/1.22

(58) Field of Classification Search
USPC ........................................................ 623/1.3
See application file for complete search history.

(56) References Cited

U.S. PATENT DOCUMENTS

| 5,383,926 | A  | * | 1/1995 | Lock et al. ..................... 623/1.2 |
| 6,241,762 | B1 | * | 6/2001 | Shanley ....................... 623/1.17 |
| 6,261,318 | B1 | * | 7/2001 | Lee et al. ..................... 623/1.15 |
| 6,264,687 | B1 | * | 7/2001 | Tomonto ...................... 623/1.16 |
| 6,425,855 | B2 | * | 7/2002 | Tomonto ......................... 600/36 |
| 6,764,507 | B2 | * | 7/2004 | Shanley et al. .............. 623/1.16 |
| 6,776,794 | B1 |   | 8/2004 | Hong et al. |
| 6,964,677 | B2 |   | 11/2005 | Osypka |
| 7,160,321 | B2 | * | 1/2007 | Shanley ....................... 623/1.42 |
| 7,179,288 | B2 | * | 2/2007 | Shanley ....................... 623/1.42 |
| 7,429,268 | B2 | * | 9/2008 | Shanley et al. .............. 623/1.15 |
| 7,909,865 | B2 | * | 3/2011 | Shanley ....................... 623/1.42 |
| 8,016,873 | B1 | * | 9/2011 | Drasler et al. ............... 623/1.15 |

(Continued)

FOREIGN PATENT DOCUMENTS

| CN | 1810315 | 8/2006 |
| DE | 101 03 000 | 8/2002 |

(Continued)

*Primary Examiner* — David Isabella
*Assistant Examiner* — Jacqueline Woznicki
(74) *Attorney, Agent, or Firm* — Michael J. Striker

(57) ABSTRACT

A medical implant for the expansion and support of a body vessel is formed as elongate struts in a shape of a tube. The struts are plastically deformable at least in sections so that the implant remains permanently expanded in the radial direction transversely to a longitudinal axis of the struts in the expanded state. A course of the expandable element has a plurality of direction changes with respect to the longitudinal axis. The expandable element has a constriction point in the contracted state designed as an intended breaking point for the expandable element. The constriction point breaks upon application of excessive force applied in the radial direction preventing further expansion of the expandable element.

15 Claims, 4 Drawing Sheets

(56) References Cited

U.S. PATENT DOCUMENTS

| | | | |
|---|---|---|---|
| 8,052,734 B2* | 11/2011 | Shanley | 623/1.15 |
| 8,439,968 B2* | 5/2013 | Shanley | 623/1.42 |
| 2001/0025130 A1* | 9/2001 | Tomonto | 600/36 |
| 2002/0010507 A1 | 1/2002 | Ehr et al. | |
| 2002/0068969 A1* | 6/2002 | Shanley et al. | 623/1.16 |
| 2002/0107562 A1* | 8/2002 | Hart et al. | 623/1.15 |
| 2003/0009214 A1* | 1/2003 | Shanley | 623/1.15 |
| 2003/0014102 A1 | 1/2003 | Hong et al. | |
| 2003/0167085 A1* | 9/2003 | Shanley | 623/1.15 |
| 2003/0199970 A1* | 10/2003 | Shanley | 623/1.16 |
| 2004/0122505 A1* | 6/2004 | Shanley | 623/1.15 |
| 2004/0236408 A1* | 11/2004 | Shanley | 623/1.16 |
| 2005/0033405 A1* | 2/2005 | Solovay | 623/1.13 |
| 2005/0203609 A1* | 9/2005 | Shanley | 623/1.15 |
| 2006/0122688 A1* | 6/2006 | Shanley et al. | 623/1.15 |
| 2006/0155364 A1* | 7/2006 | Holloway et al. | 623/1.16 |
| 2008/0177373 A1* | 7/2008 | Huang et al. | 623/1.15 |
| 2008/0243070 A1* | 10/2008 | Shanley | 604/103.1 |
| 2010/0131044 A1 | 5/2010 | Patel | |
| 2011/0060401 A1 | 3/2011 | Hoerstrup et al. | |
| 2012/0071963 A1* | 3/2012 | Shanley | 623/1.16 |

FOREIGN PATENT DOCUMENTS

| | | |
|---|---|---|
| DE | 101 05 160 | 8/2002 |
| EP | 1 958 598 | 8/2008 |
| WO | 2008/008291 | 1/2008 |

* cited by examiner

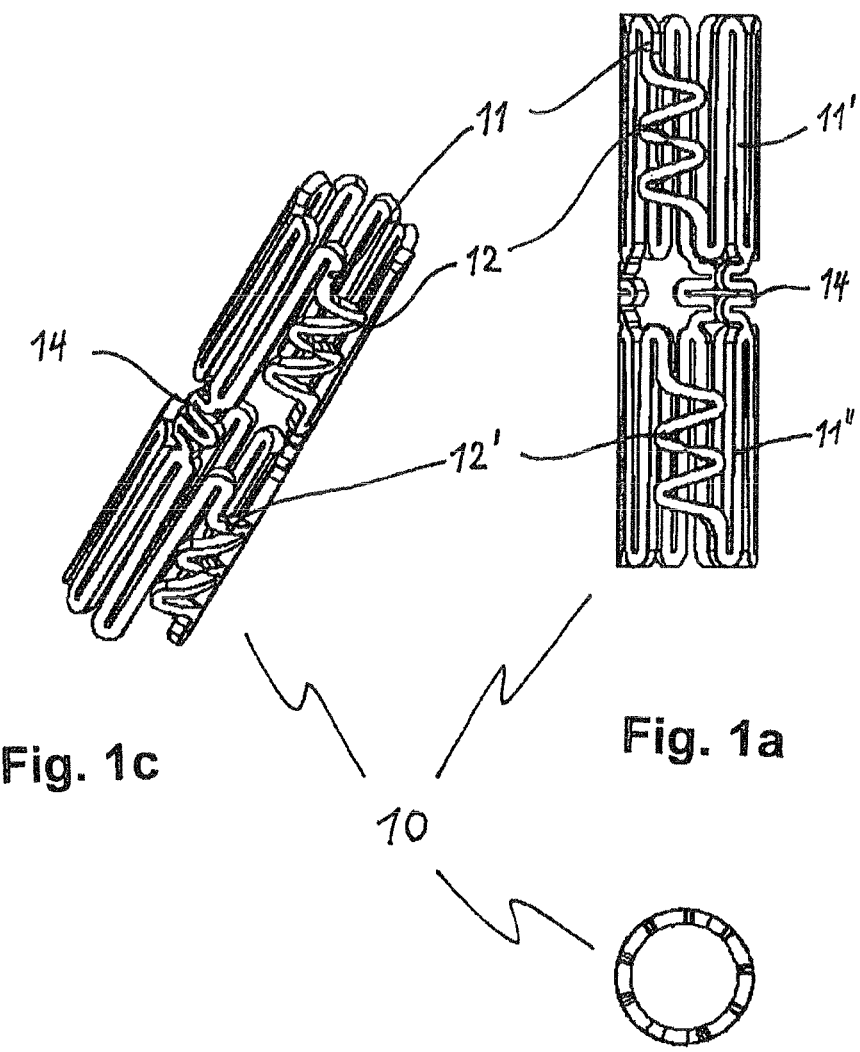
Fig. 1c
Fig. 1a
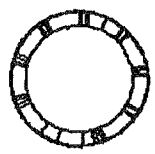
Fig. 1b

STENT HAVING EXPANDABLE ELEMENTS

CROSS-REFERENCE TO RELATED APPLICATION

The invention described and claimed hereinbelow is a National Stage Application of PCT/DE 2006/001306, filed Sep. 16, 2009, under 35 USC §371 (the PCT application). The PCT application, whose subject matter is incorporated herein by reference, provides the basis for a claim of priority of the invention under 35 U.S.C. 119(a)-(d).

BACKGROUND OF THE INVENTION

The invention relates to a medical implant for the expansion and support of a body vessel from the inside thereof (="stent"), which can be inserted into the body vessel in a contracted state preferably in a minimally invasive manner, positioned there and transferred into an expanded state, wherein the implant is designed in the shape of a tube having elongate struts which form a wall of the implant, and wherein the struts are plastically deformable at least in sections in such a way that the implant remains permanently expanded in the radial direction transversely to the longitudinal axis of the struts in the expanded state Such stents have been known for a long time, for example, from DE 101 05 160 B4.

Such a stent has a geometric structure, at least, that enables it to be transferred from the contracted state thereof into an expanded state (="redilation"), usually through a plurality of stages. The inner cross section of the stent can be expanded only to a predetermined maximum dimension, however, starting from the original minimum cross section. Further radial dilation is not possible because the stent would otherwise deform in an undefined manner and then break. A certain stent size is therefore manufactured and used for every vessel size to ensure that the radial holding force of the stent is optimal in the particular application.

Expansion groups that have been possible and common so far provide cross-sectional expansions of the stent (measured in millimeters of the inner diameter) to 4 to 6, to 6 or 8, to 8 or 10, to 10 or 12. Even greater expansions are unusual and are typically used only in special applications, although it is assumed that starting cross sections and minimum cross sections are much greater, that is, expansions from 16 mm to 20 mm in diameter.

One of the main problems associated with the use of such stents is the application in young children, in particular in the field of pediatric and neonatal cardiology: In this case, stents having very small starting cross sections must always be used initially due to the small vessel sizes of the young patients. However, the child then grows into an adolescent and ultimately into an adult, the vessels increase in size enormously with respect to the point in time of initial implantation, and the maximum expandability of the stent that was used is reached very quickly, and therefore the stent usually must be replaced by a larger model at least once. This replacement requires surgery every time, of course, which is very stressful for the growing patient even if minimally invasive techniques can be used.

SUMMARY OF THE INVENTION

The problem addressed by the present invention is that of improving a generic arrangement of the initially described type having the simplest technical means possible, in a manner that is not complex and is cost-favorable, such that a range of expansions of the cross section of the tubular implant in the radial direction from the minimally contracted original state to the maximum redilated final state that is very considerably greater than the previous design-related maximum dimension of redilation is made possible, which ultimately enables a stent that has been inserted in childhood to remain in the patient's body—if medically possible—until adulthood ("a pediatric stent that grows with the patient").

According to the invention, this problem is solved in a manner that is as surprisingly simple as it is effective in that at least one of the struts comprises an expandable element that forms a strut section within said strut, in which the expandable element extends partially geometrically transversely to the longitudinal axis of the strut in the contracted state, the course of the expandable element having a plurality of direction changes with respect to said longitudinal axis, and that the material, thickness and strut width of the expandable element are selected such that, by applying force in the radial direction of the tubular implant, the expandable element can be transferred by way of plastic elongation into a permanently expanded state in which the strut section forming the expandable element has a greater geometric extension transversely to the longitudinal axis and a smaller extension in the direction of the longitudinal axis than in the contracted state. Redilations in a very wide range can be achieved as a result, which are very considerably greater than the previous design-related maximum dimension of conventional stents.

Very particularly preferred are embodiments of the implants according to the invention, in which the expandable element is designed by way of the material properties and geometry thereof such that an expansion of the cross section of the tubular implant in the radial direction from the minimally contracted state to the maximally redilated state from 2 mm to 18 mm, preferably from 4 mm to 16 mm, or from 6 mm to 24 mm, preferably from 6 mm to 20 mm, is made possible. It is therefore possible to cover the ranges of human growth from childhood to adulthood which normally occur in practical applications.

A class of embodiments of the implant according to the invention that is particularly simple in terms of production engineering and can be made compact is characterized in that the expandable element has a geometric course having a zigzag, serpentine and/or meandering shape, at least in sections, in the contracted state. Depending on the number of zigzag structures—which can be advantageously disposed in opposing directions—the expandability of the stent can become rather great compared to conventional stents according to the prior art in particular. A stent according to the invention having expandable elements shaped in this manner also has a particularly great radial force due to this structure, independent of the redilation stage.

Another class of embodiments of the invention in which the expandable element has a geometric course having a spiral shape, at least in sections, in the contracted state proves successful in practical application, however.

Developments are particularly advantageous that are characterized in that the expandable element has the geometric shape of a double spiral, at least in sections, in the contracted state, which curves in two opposing directions of rotation starting from a common midpoint.

Developments of these embodiments are possible in which the spirals have an outer contour that is round, in particular circular, or triangular or quadrangular, in particular square.

In embodiments of the implant according to the invention, the expandable element has a constriction point in the contracted state, the strut width of which is smaller than the strut widths of the adjacent strut sections.

Advantageous developments of these embodiments are characterized in that the strut width of the constriction point is at most two-thirds as great, preferably half as great, as the strut widths of the adjacent strut sections.

Very particularly preferred are developments in which the constriction point is designed as an intended breaking point for the expandable element, which breaks if excessive force is applied in the radial direction of the tubular implant, creating a further possibility for redilation and thereby preventing further expansion of the expandable element. In this case, the particular strut of the implant is then interrupted in the longitudinal direction. Despite this interruption, it is not necessary to implant a new stent in most practical applications since the treated vessel has usually stabilized to a sufficient extent after such a growth period, and therefore the remaining, broken stent suffices as support.

As already known per se from the prior art, connecting elements can be disposed between pairs of struts which are adjacent to one another in the direction of the longitudinal axis of the implant, which, when force is applied in the longitudinal direction of said struts, induce permanent plastic enlargement of the implant in the axial direction.

An embodiment of the implant according to the invention is preferable in which a plurality of expandable elements is provided for each stent, thereby increasing the flexibility and range of applications of the implant.

In a class of developments of this embodiment, the expandable elements all have the same mechanical properties and, in particular, have the same geometric design, thereby enabling a uniform manufacturing process to be used.

Alternatively, in another class of developments, the expandable elements can all have different mechanical properties. This makes it possible to provide a large bandwidth of designs of the implants according to the invention that are individually adapted to the patient's special problems.

The different mechanical properties of the expandable elements can be achieved, in variants of these developments, by providing the expandable elements with the same geometric design—which is favorable for a uniform manufacturing process—but with different strut widths.

However, another variant of the invention is characterized in that the expandable elements have different geometric designs. In turn, this results in a large variety of different designs of the implants that are tailored for individual solutions to problems.

In preferred developments of the embodiment described above, a plurality of expandable elements can be disposed one behind the other in the longitudinal direction of the implant.

Variants are also advantageous in which a plurality of expandable elements are distributed azimuthally, in particular symmetrically, around the circumference of the implant.

Very particularly preferred are embodiments of the implant according to the invention in which the struts, including the expandable elements, are produced from a tubular original piece, preferably by way of laser cutting. As a result it is also possible to create particularly fine structures and contours in reproducible quality, even in large quantities.

The implant according to the invention can be made of a material utilizing chrome and/or cobalt and/or platinum and/or an alloy of these materials and/or a stainless steel alloy, at least in the region of the expandable element.

It is also advantageous for many applications when the implant is made of a material having memory effect, in particular Nitinol, at least in the region of the expandable element, which undergoes a defined structural change due to the effect of heat, for instance, and retains said structural change if the thermal conditions are maintained.

Parts of the implant, at least, can also be made of made of biocompatible plastics, in particular silicone or polytetrafluorethylene (PTFE), and/or of fibrous composite materials, in particular carbon fibers.

Moreover, titanium and/or gold and/or tantalum and/or an alloy of these metals are also feasible for use as materials for the implant according to the invention, or at least parts thereof.

For special applications it can also be useful, however, to produce parts of the implant, at least, out of a ceramic material.

Finally, embodiments of the invention are also advantageous that are characterized in that a biologically active coating, in particular a growth-inhibiting and/or growth-promoting and/or antibacterial coating, is provided on the surface of the implant, at least in sections.

Further features and advantages of the invention will become apparent from the detailed description of embodiments of the invention presented below with reference to the figures in the drawing which shows the details that are essential to the invention.

Further features and advantages of the invention will also become apparent from the claims. The individual features may be implemented individually, or they may be combined in any possible manner to form variants of the invention.

BRIEF DESCRIPTION OF THE DRAWINGS

Example embodiments of the invention are depicted in the schematic drawing and are described in greater detail in the description that follows.

Shown are.

DESCRIPTION OF THE PREFERRED EMBODIMENTS

Figure 1D:
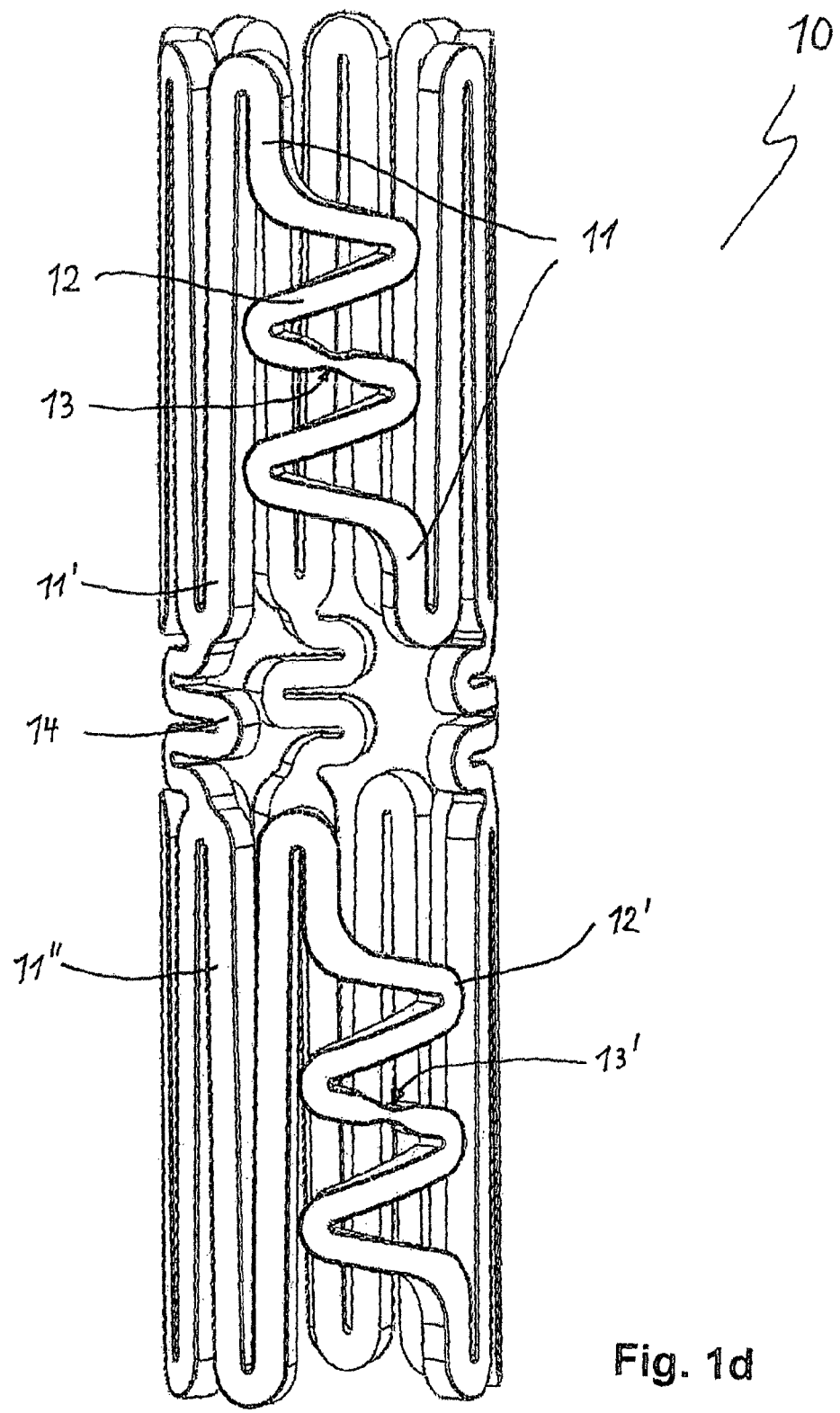
FIGS. 1$a$-$d$ an embodiment of the implant according to the invention having two serpentine expandable elements disposed one behind the other in the longitudinal direction, in a schematic spatial depiction, namely 1$a$) from the side, 1$b$) from above in the longitudinal direction of the struts, 1$c$) spatially at a slant, and 1$d$) enlarged, from the side.

The embodiments of the medical implant 10; 20 according to the invention, which are depicted schematically in the figures of the drawing, for expanding and supporting a body vessel from the inside thereof (="stent"), are each designed in the shape of a tube having elongate struts 11,11',11"; 21,21', 21" which form a wall of the implant 10; 20 and are plastically deformable at least in sections in such a way that the implant 10; 20 remains permanently expanded in the radial direction transversely to the longitudinal axis of the struts 11,11',11"; 21,21',21" after redilation. To achieve expandability of the implant 10; 20 that is considerably greater than that of known stents, at least one of the struts 11; 21 comprises an expandable element 12,12'; 22; 32$a$,32$b$,32$c$ which forms a strut section within said strut 11; 21, in which the expandable element 12,12'; 22; 32$a$,32$b$,32$c$ extends partially geometrically transversely to the longitudinal axis of the strut 11; 21 in the contracted state, the course of the expandable element 12,12'; 22; 32$a$,32$b$,32$c$ having a few direction changes with respect to said longitudinal axis. The material, thickness and strut width of the expandable element 12,12'; 22; 32a,32b,32c are selected such that, by applying force in the radial direction of the tubular implant 10; 20, the expandable element 12,12'; 22; 32a,32b,32c can be transferred by way of plastic elongation into a permanently expanded state in which the strut section forming the expandable element 12,12'; 22; 32a,32b, 32c has a greater geometric extension transversely to the longitudinal axis and a smaller extension in the direction of the longitudinal axis than in the contracted state.

A feature common to all the embodiments of the invention depicted in the drawing is also that each of the expandable elements 12,12'; 22; 32a,32b,32c comprises a constriction point 13,13'; 23; 33a,33b,33c designed as an intended breaking point, which breaks if excessive force is applied in the radial direction of the tubular implant 10; 20, creating a further possibility for redilation and thereby preventing further expansion of the expandable element 12,12'; 22; 32a,32b, 32c.

Figure 2:
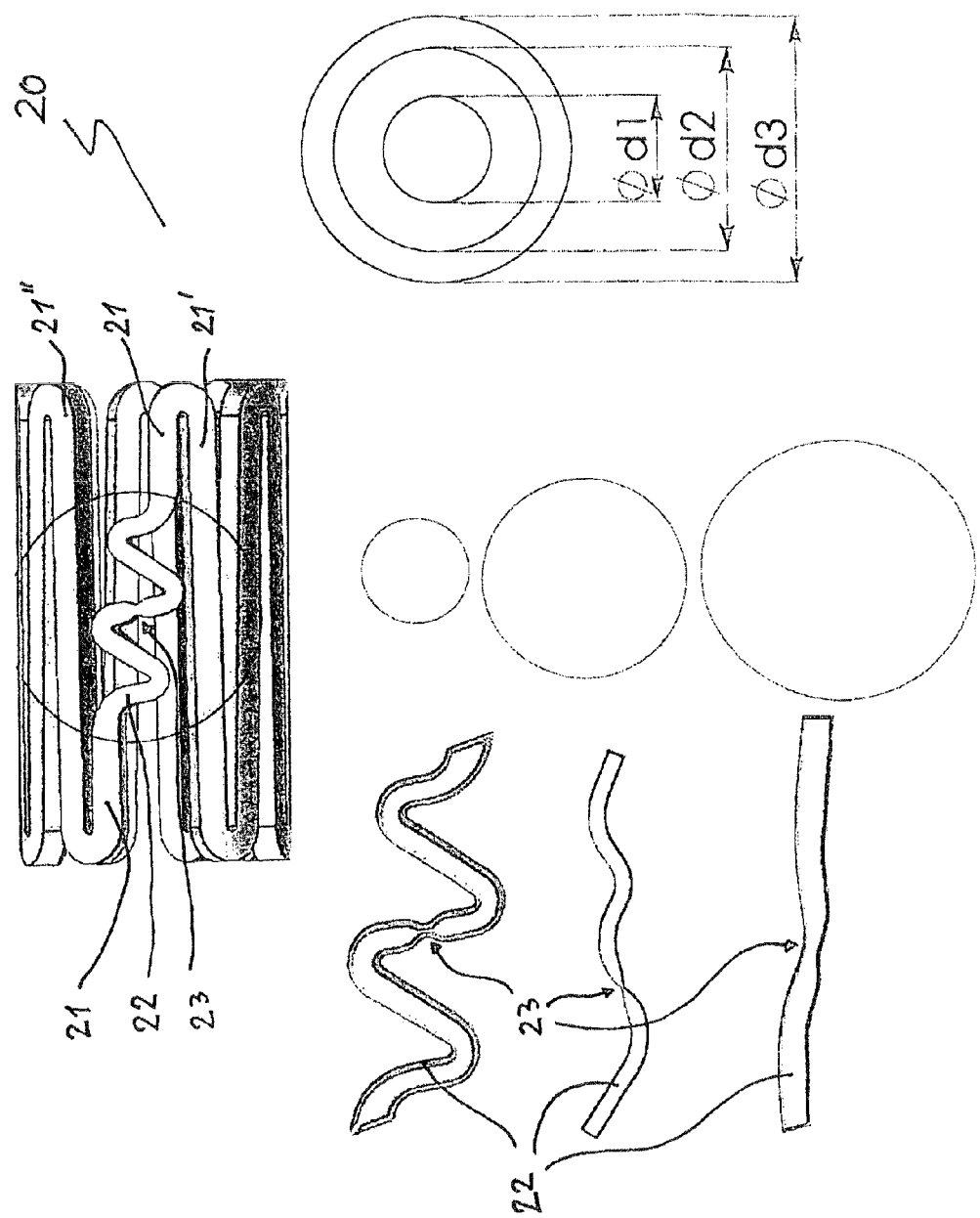
FIG. 2 an embodiment comprising only one expandable element, and various phases of the expansion of the implant, shown in detail.
Figure 3A:
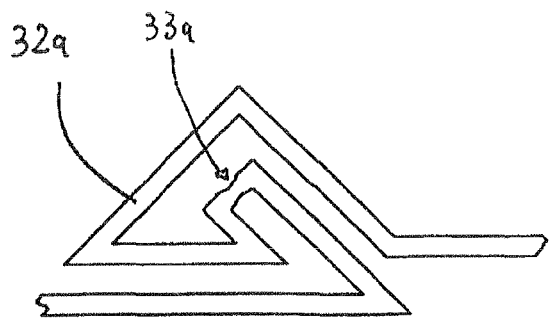
FIGS. 3$a$-$c$ embodiments of expandable elements according to the invention in the form of double spirals, namely 3$a$) triangular, 3$b$) round and 3$c$) quadrangular.
Figure 3B:
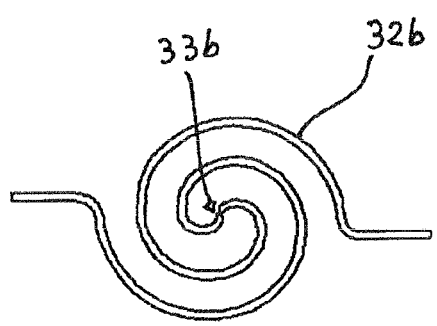
Figure 3C:
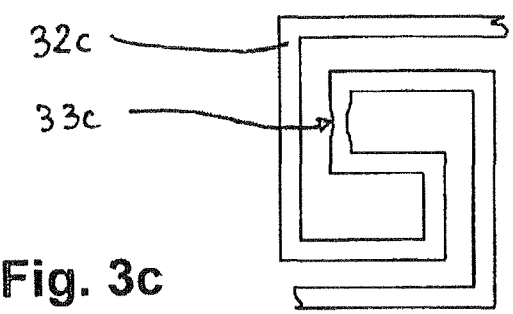

The expandable elements 12,12'; 22 depicted in FIGS. 1a to 2 each have a serpentine geometric course, while the embodiments of expandable elements 32a, 32b, 32c according to the invention, which are depicted highly schematically in FIGS. 3a to 3c, each have the geometric course of a double spiral which curves in two opposing directions of rotation starting from a common midpoint. In the example embodiment depicted in FIG. 3a, said double spiral is triangular, and is round in FIG. 3b and quadrangular in FIG. 3c. Other geometric shapes are also feasible, such as zigzag or meandering courses of the expanded elements instead of the rounded serpentine shapes, although they are not depicted in the drawing.

The embodiment depicted in FIGS. 1a to d is also characterized in that a plurality of expandable elements 12, 12'—exactly two in this case—are disposed one behind the other in the longitudinal direction of the implant 10. They have the same geometric design in the present embodiment, and can have the same or different mechanical properties.

In this embodiment, connecting elements 14 are disposed between a few pair of struts 11', 11" adjacent to one another in the direction of the longitudinal axis of the implant 10, which induce permanent plastic enlargement of the implant 10 in the axial direction when force is applied in the longitudinal direction of said struts 11', 11". These connecting elements 14 therefore perform a completely different function than the expandable elements 12, 12' according to the invention, and they also do not form a strut section within any of the struts 11, 11', 11". Instead, they are disposed axially between adjacent struts 11', 11" and are incapable of inducing a radial expansion of the implant 10, and are only capable of inducing an axial extension.

In embodiments of the implant according to the invention, which are not depicted in the drawing, it is also possible for a plurality of expandable elements to be distributed azimuthally around the circumference of the implant.

FIG. 2 shows three different phases of expansion using a simple embodiment having only one—serpentine—expandable element 22 in the strut 21 of the implant 20:

In the original, maximally contracted state in which the implant 20 is introduced into the vessel of the patient, the serpentine lines of the expandable element 22 still extend in relatively long sections transversely to the longitudinal direction of the segments 21, 21' 21". Accordingly, a minimum diameter d1 results and, therefore a minimum inner cross section of the implant 20 at this point.

After force is applied in the radial direction, the expandable element 22 expands, as intended, and the serpentine lines are "stretched" and now extend transversely to the longitudinal direction only in short sections. The diameter d2 and, therefore, the inner cross section of the implant 20 are increased considerably.

Finally, in the third phase, the expandable element 22 is stretched such that the serpentine lines practically become straight lines. The maximum diameter d3 results and, therefore, the greatest inner cross section of the implant 20. If additional force is applied, the constriction point 23, which is designed as an intended breaking point, breaks in a defined manner.

The expandable element according to the invention should be designed by way of the material properties and geometry thereof such that a greatest possible expansion of the inner cross section of the tubular implant in the radial direction from the minimally contracted state to the maximally redilated state is made possible. Expansions of an original diameter d1 from 1.3 mm to a maximum diameter d3 of 18 mm or from d1=2 mm to d3=24 mm are realistic. In practical application, however, expansions of d1=3 mm to d3=20 mm will suffice. Expandability of the stent to a multiple of the original diameter is therefore achieved.

The implants 10; 20 according to the invention, in particular the struts 11,11',11"; 21,21',21", including the expandable elements 12,12'; 22; 32a,32b,32c, are preferably produced from a tubular original piece by way of laser cutting.

It can also be advantageous for the implant according to the invention to be provided with a biologically active coating, in particular a growth-inhibiting and/or growth-promoting and/ or antibacterial coating, on the surface thereof, at least in sections.

What is claimed is:

1. A medical implant for insertion in a minimally invasive manner into a position of a body vessel in a contracted state and then transformed into a radially expanded state for expansion and support of the body vessel from an inside thereof, the medical implant comprising:

a tubular body having a tube longitudinal axis, the tubular body configured with elongate struts that extend along the tube longitudinal axis and that form a wall of the implant, wherein the struts are plastically deformable at least in sections, by which plastically deformable sections, the implant remains permanently radially expanded transversely to the tube longitudinal axis in the expanded state;

wherein at least one of the struts comprises an expandable element that forms one of the plastically deformable sections and that extends partially geometrically transversely to the tube longitudinal axis in the contracted state, wherein a course of the expandable element has a plurality of direction changes with respect to the tube longitudinal axis, wherein a material, a thickness and a strut width of the expandable element are selected such that applying force to the expandable element in a radial direction with respect to the tube longitudinal axis transforms the expandable element by plastic elongation into a permanently expanded state in which the strut section has a greater radial extension transversely to the tube longitudinal axis and a smaller axial extension with the tube longitudinal axis than in the contracted state, wherein the expandable element has a single constriction point in the contracted state that is designed as an intended breaking point for the expandable element, the single constriction point having a strut width that is two-thirds or less than strut widths of adjacent strut sections of the expandable element and configured to break where excessive force is applied in the radial direction of the tubular implant, allowing for redilatation and thereby preventing further expansion of the expandable element, and wherein a length of the tubular body is formed by pairs of the elongate struts that are each arranged longitudinally adjacent to each other and interconnected by connecting elements that respond to force applied in a direction coaxial with the tube longitudinal axis to induce permanent plastic enlargement of the implant axially.

2. The implant according to claim 1, wherein material properties and geometry of the expandable element limit expansion of the tubular implant in the radial direction in a range from a minimally contracted state to a maximally redilated state and wherein the range is selected from ranges within a group consisting of: 2 mm to 18 mm, 4 mm to 16 mm, 6 mm to 24 mm and 6 mm to 20 mm.

3. The implant according to claim 1, wherein the course of the expandable element has at least one of a zigzag, a serpentine or a meandering shape, at least in sections, in the contracted state.

4. The implant according to claim 1, wherein the course of the expandable element has a spiral shape in the contracted state.

5. The implant according to claim 4, wherein the expandable element has a shape of a double spiral in the contracted state, which curves in two opposing directions of rotation starting from a common midpoint.

6. The implant according to claim 4, wherein the spiral shape has an outer contour that is round, triangular or quadrangular.

7. The implant according to claim 1, wherein the strut width of the single constriction point is at most half as great as the strut widths of the adjacent strut sections.

8. The implant according to claim 1, wherein the at least one of the struts includes a plurality of the expandable elements forming the plastically deformable sections.

9. The implant according to claim 8, wherein the expandable elements are identical.

10. The implant according to claim 8, wherein the expandable elements have material properties and geometry that limit expansion of the tubular implant in the radial direction in a range from a minimally contracted state to a maximally redilated state and wherein the material properties are different.

11. The implant according to claim 10, wherein the expandable elements have a same geometric design but different strut widths.

12. The implant according to claim 10, wherein the expandable elements have different geometric designs.

13. The implant according to claim 8, wherein each of the expandable elements is disposed one behind the other in the tube longitudinal direction.

14. The implant according to claim 8, wherein each of the expandable elements is distributed azimuthally around a circumference of the implant.

15. The implant according to claim 8, wherein the struts, including the expandable elements, are laser cut from a tubular original piece.

* * * * *